United States Patent [19]
Kalidini

[11] Patent Number: 5,337,620
[45] Date of Patent: Aug. 16, 1994

[54] SAMPLING TOOL

[76] Inventor: Sanyasi R. Kalidini, 8303 Hana Rd., Edison, N.J. 08817

[21] Appl. No.: 70,281

[22] Filed: Jun. 2, 1993

[51] Int. Cl.⁵ ............................................. G01N 1/12
[52] U.S. Cl. ................................................. 73/864.64
[58] Field of Search ..................... 73/864.63–864.67, 73/863.31

[56] References Cited

U.S. PATENT DOCUMENTS

| | | | |
|---|---|---|---|
| 2,185,651 | 1/1940 | Sollie | 73/864.64 |
| 2,875,615 | 3/1959 | Ulvin | 73/864.64 |
| 2,968,781 | 1/1961 | Archer et al. | |
| 3,080,760 | 3/1963 | Piersma | 73/864.64 |
| 3,575,055 | 4/1971 | Thornton, Jr. | |
| 3,595,088 | 4/1971 | Meunier | |
| 3,875,803 | 4/1975 | Clewlow | |
| 3,943,771 | 3/1976 | Hanoa et al. | |
| 4,022,065 | 5/1977 | Ramin et al. | |
| 4,055,088 | 10/1977 | Dias | |
| 4,082,003 | 4/1978 | Hentschel, Jr. et al. | |
| 4,283,946 | 8/1981 | Bowser et al. | |
| 4,361,052 | 11/1982 | Nicol et al. | |
| 4,442,721 | 4/1984 | Singer | |
| 4,518,076 | 5/1985 | Feisel et al. | |
| 4,580,577 | 4/1986 | O'Brien et al. | |
| 4,641,504 | 2/1987 | Ellis | |
| 4,660,423 | 4/1987 | Armstrong et al. | 73/864.66 |
| 4,744,256 | 5/1988 | Niskin | 73/864.64 |
| 4,790,198 | 12/1988 | Awtry et al. | 73/864.64 |
| 4,951,511 | 8/1990 | Perron et al. | |

FOREIGN PATENT DOCUMENTS

| | | | |
|---|---|---|---|
| 285639 | 12/1990 | Fed. Rep. of Germany | |
| 484331 | 11/1954 | Italy | 73/864.64 |
| 204682 | 10/1967 | U.S.S.R. | |

*Primary Examiner*—Robert Raevis
*Attorney, Agent, or Firm*—Richard C. Litman

[57] ABSTRACT

A sampling tool or sampling thief having a number of removable sampling dies that can be placed within a receiving rod. These dies have cavities disposed therein defining varying volumes. The receiving rod comes in sections that can be mutually engaged to provide a rod of any length. The rod and the attached dies are then placed within a hollow outer tube containing apertures that are aligned relative to the cavities such that the rod and dies are manipulable into a position where the material to be sampled can enter the cavities through the apertures in the outer tube after the device is inserted into a powder blender or similar apparatus. As an alternative to the variously sized cavities, a die can be provided where the cavity is adjustable through a threaded adjustment or the like. The sampling thief is particularly useful for sampling pharmaceutical powder blends.

9 Claims, 4 Drawing Sheets

SAMPLING TOOL

BACKGROUND OF THE INVENTION

1. Field of the Invention

The present invention relates to sampling and measuring. More specifically, it relates to sampling precise volumes of powder blends, especially pharmaceutical powder blends. Even more specifically, it relates to a sampling device or sampling thief, wherein sampling dies having cavities of varying, specific volumes can be placed within receiving areas in sampling rods. The rods and the dies disposed therein are then placed within an outer tube that includes apertures that are rotatably alignable with the receiving areas and, thus, the cavities in the dies. The entire device then can be inserted into a powder blend and the inner sampling rods are rotated such that the outer apertures are aligned with the cavities in the dies, allowing predetermined volumes of the powder to be collected. The inner rods are then rotated such that the apertures in the outer tube are no longer aligned with the cavities, and the device is withdrawn from the powder, the outer tube removed, and the dies withdrawn from the sampling rods, and the powder samples removed for testing purposes.

2. Description of the Prior Art

In the manufacturing of solid dosage form pharmaceuticals, one of the steps is blending different active and inactive ingredients in a blender. Such powder blends are routinely sampled for testing of content uniformity. A proper sampling technique requires unit-dose sampling from different areas of the blender, for example, top, middle and bottom of a blender. Unit-dose sampling is defined herein as taking just enough of an amount of the powder blend to provide one dose of the active ingredient. This proves to be a difficult task in the pharmaceutical industry because of the large number of products with varying doses and bulk densities and different sized blenders used. This requires several sampling thieves that are currently available, increasing the cost to the manufacturer. The present invention overcomes this drawback by providing: (1) a sampling device where a variety of different dies, each one having a cavity of precise volume, are interchangeable within the apparatus; (2) as an alternative, an adjustable volume die; and (3) a sampling rod structure in sections, providing the flexibility of sampling rod length.

A number of patents have been issued that address sampling of various materials. These will be discussed in order of their perceived relevance to the claimed invention.

In the German patent document DD 285,639 A5 published on Dec. 19, 1990 to Rolf Hoffman et al. there is disclosed a sampling device where the chamber is rotatable to receive and discharge a sample.

In USSR patent 204,682 issued on Jul. 28, 1967 to G. K. Kushchanov there is disclosed a sampler that discloses a pipe having inclined shelves. The pipe is disposed within a cylindrical body having ports and gates to allow samples to be collected as the device is axially rotated.

In U.S. Pat. No. 2,968,184 issued on Jan. 17, 1961 to James R. Archer et al. we see a sampling tube having a receiving member and a cover member. The cover member is slidable relative to the receiving member which is in the form of a tube and has holes cut therein. Thus, the device can be inserted into a material to be sampled and the cover is slid back to allow the material to enter the holes in the receiving member. The cover is then slid back into a closed position and the device is withdrawn.

In U.S. Pat. No. 4,442,721 issued on Apr. 17, 1984 to Laura G. Singer there is disclosed a moisture and consistency soil sampler. This comprises an elongate member with en insertable end, a handle end, and a plurality of generally transverse collecting means disposed proximate the insertable end that define soil collecting pockets.

The last patent to be discussed in detail is U.S. Pat. No. 4,518,076 issued on May 21, 1985 to Armin Feisel et al. In this document there is shown a workpiece pallet tray with plastic insert holders. Inserts are provided that snap fit into the holding areas in the tray.

Other patents that disclose apparatus for sampling various materials are listed below.

| U.S. Pat. No. | INVENTOR | DATE OF ISSUE |
| --- | --- | --- |
| 3,575,055 | Thornton, Jr, | April 13, 1971 |
| 3,595,088 | Meunier | July 27, 1971 |
| 3,875,803 | Clewlow | April 8, 1975 |
| 3,943,771 | Handa et al. | March 16, 1976 |
| 4,022,065 | Ramin et al. | May 10, 1977 |
| 4,055,088 | Dias | October 25, 1977 |
| 4,283,946 | Bowser et al. | August 18, 1981 |
| 4,361,052 | Nicol et al. | November 30, 1982 |
| 4,580,577 | O'Brien et al. | April 8, 1986 |
| 4,641,540 | Ellis | February 10, 1987 |
| 4,951,511 | Perron et al. | August 28, 1990 |

None of the above inventions and patents, taken either singly or in combination, is seen to describe the instant invention as claimed.

SUMMARY OF THE INVENTION

The present invention is a sampling tool having a number of removable sampling dies that can be placed within a receiving rod. These dies have cavities therein of varying volumes. The rod and the attached dies are then placed within a hollow outer tube containing apertures that are aligned relative to the cavities such that the rod and dies are manipulable into a position where the material to be sampled can enter the cavities through the apertures in the outer tube after the device is inserted into a powder blender or the like. In an alternative to the variously sized cavities, a die can be provided where the cavity is adjustable through a threaded adjustment or the like.

Accordingly, it is a principal object of the invention to provide a sampling tool wherein various predetermined volumes of a material can be obtained by placing dies having variously sized cavities within a receiving rod, inserting the dies and the rod into a hollow tube containing apertures, and then, by manipulating the receiving rod and dies relative to the apertures, allow the cavities to fill with the desired volume of material.

It is another object of the invention to provide a sampling tool wherein the receiving rods are mutually engageable to allow for the length, and thus the number of samples taken, to vary according to the user's needs.

It is a further object of the invention to provide a sampling tool wherein the dies are held snugly and securely in the receiving rod and to prevent accidental spillage during removal of the dies.

Still another object of the invention is to provide a sampling tool wherein an adjustable die can be provided, if desired, for providing varying volumes or for reducing the number of dies needed on hand.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
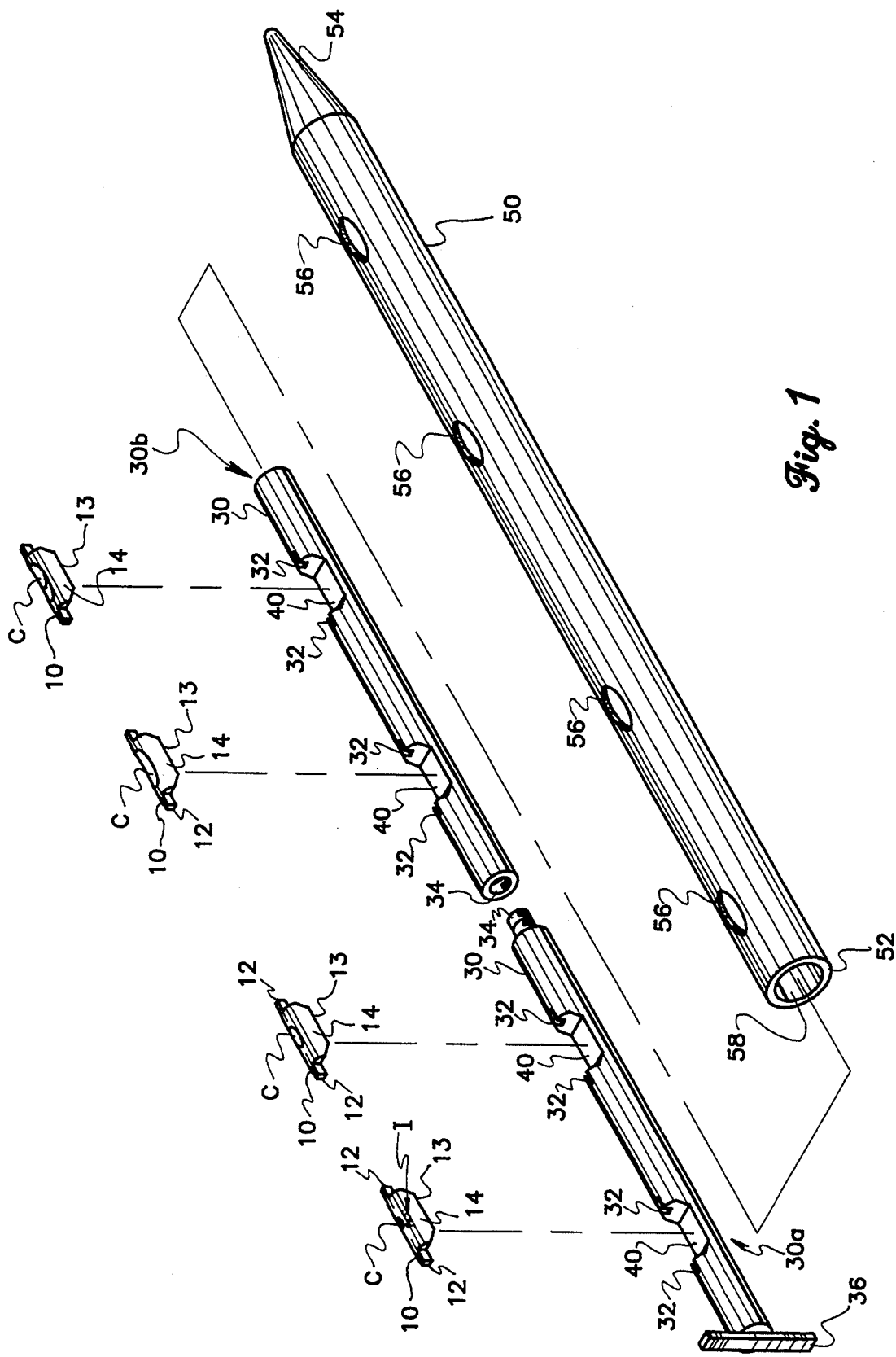
FIG. 1 is an exploded perspective view of the preferred embodiment of the sampling tool.
Figure 2:
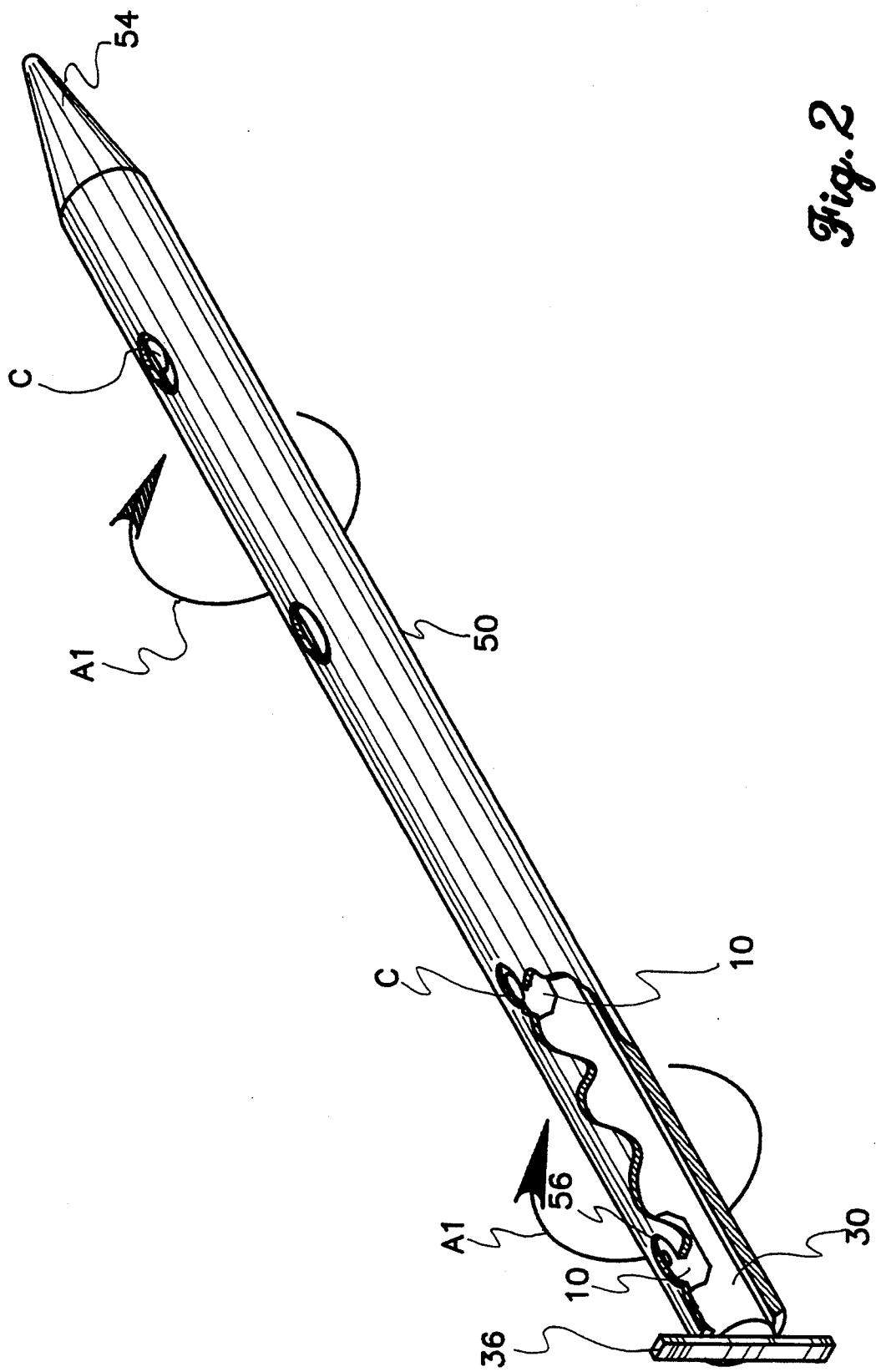
FIG. 2 is a partial cutaway view of the sampling tool showing the alignment of the outer apertures and the cavities within the dies.

Referring to FIGS. 1 and 2, the preferred embodiment of the sampling tool is shown. The device has a plurality of dies 10, a die receiving means 30, which is generally rod-shaped and has multiple interengageable portions, and a sample access means 50 that is in the shape of a hollow tube with one open end 52 and one tapered end 54.

Referring now to FIG. 1 it can be seen that the dies 10 have a number of differently sized cavities C. These cavities are dimensioned so that they hold a very precise volume of material. As can be seen in FIG. 1, the dies also may have indicia I on their surfaces to show the user the volume that they can contain. This volume would preferably be measured in cubic centimeters. In the preferred embodiment, each die 10 has a flat bottom 13 that allows it to be placed on a surface, such as a lab table or the like, without the likelihood of inadvertent spilling. This bottom 13 matches the flat receiving surface 40 on the die receiving means 30. Additionally, the dies 10 have a pair of ears 12 that correspond to the pair of slots 32 in the die receiving means 30. The cooperation of the ears 12 and the slots 32 prevents lateral movement of the dies 10 when they are placed in the receiving means 30. This configuration also allows for grasping surfaces 14 on the sides of the dies 10 for ease in manipulation of the dies 10 into and out of the receiving means 30. Alternatively, the die receiving means 30 may have cavities instead of slots 32 to accept the dies, in which case the ears 12 are not necessary.

Turning now to the receiving means 30, these are seen to be substantially cylindrical, in the preferred embodiment. The receiving means shown are in the two sections 30a, 30b. In this preferred embodiment, the sections are approximately one foot long. The sections 30a and 30b are mutually engageable by a threaded engagement means 34. Note that though only the two sections 30a and 30b are shown, a smaller or larger number of these sections could be used, depending on the length of the sampling tool desired, or the number of samples that were desired. Also note that though threaded engagement means 34 are shown, a number of other common engagement means could be used. Located at one end of section 30a of the receiving means is the manipulable die displacement means, which, preferably, is in the form of a handle 36. This handle 36 could be permanently attached to one of the die receiving means 30 or it could be removable to make the apparatus more modular.

Once the volumes desired are chosen and the dies 10 are in place on the receiving means 30, they are placed within the sample access means 50 which is seen to be a generally cylindrical hollow tube with an interior wall 58 having a diameter dimensioned such that it smoothly and snugly receives the dies 10 and the receiving means 30. The tapered end 54 functions as a die receiving means travel stop in that the reduced diameter at that point holds the receiving means 30 in a predetermined relationship such that the cavities C and the apertures 56 on the hollow tube 50 are aligned, as best seen in FIG. 2. The receiving means 30, and the dies 10 can then be rotated using the handle 36, as indicated by the arrow A1 (seen in FIG. 2) into a first position such that the cavities C are misaligned with the apertures 56. The device is now ready to be inserted into a powder blender (not shown) or a like object containing an amount of some material which the user is desirous to sample. Once the device is inserted, the handle 36 is then used to again rotate the receiving means 30 and the dies 10 as mentioned above into a second position in which the cavities C and the apertures 56 are aligned to allow the material to be sampled (not shown) to enter the cavities. It is noted here that the apertures 56 are dimensioned such that they are smaller than the dies 10, to hold the dies 10 securely in place inside the hollow tube 50 when the cavities C and the apertures 56 on the hollow tube 50 are aligned to receive samples. The handle is then used to rotate the dies 10 and receiving means 30 back to the first position discussed above for the removal of the device from the sampling area. Thus, precise volumes are obtained within the various cavities C, and the dies 10 are easily removed from the receiving means 30 for testing.

It should be emphasized that, though in the embodiment discussed here only two section 30a and 30b are shown, any number of these sections could be engaged with one another, leading to a sampling tool of three, four, or more feet in length. All that would be required is to have an outer tube 50 with a corresponding length. It should also be noted that though a handle 36 is shown as the manipulating member, any number of appropriate shapes such as a ring or other curved shape could be used in its place to facilitate the manipulation of the device from the first to the second positions discussed above.

Figure 3:
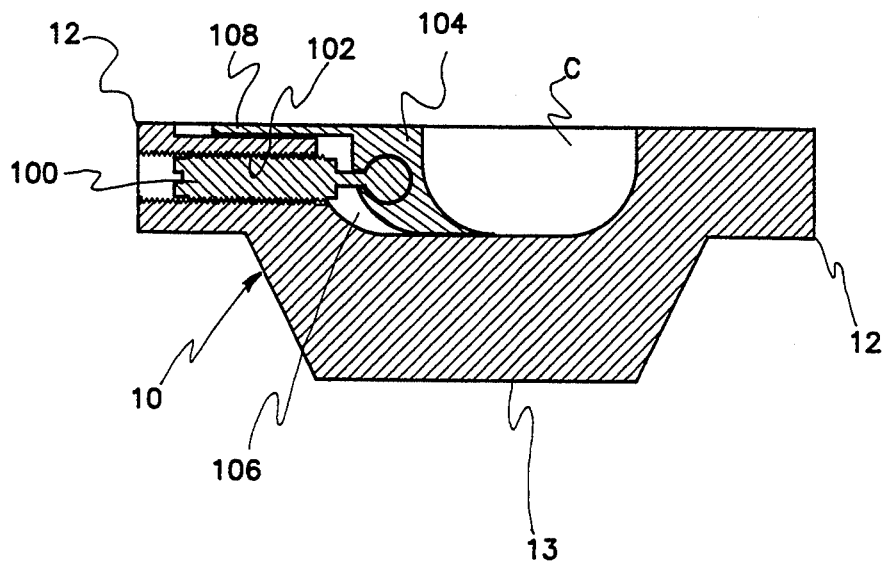
FIG. 3 is a longitudinal cross section view of an alternative die having an adjustable cavity.

Turning to FIG. 3, an alternative type of die 10 is shown. In this embodiment, the volume contained by the cavity C is adjustable. There is an adjustment that includes a threaded set screw 100 engaging threading on the set screw receiving bore 102. This moves the adjustable cavity wall 104 into the desired position to provide a specified volume of sampled material. To prevent any material from falling into the space 106 behind the adjustable cavity wall 104, there is a shield 108 integrally attached to the wall 104. It should also be noted that a die could be made that had no cavities whatsoever, being, in effect, a blank that would just take up space if only a limited number of samples were required or if a very long sampling tool assembly were contemplated.

Figure 4:
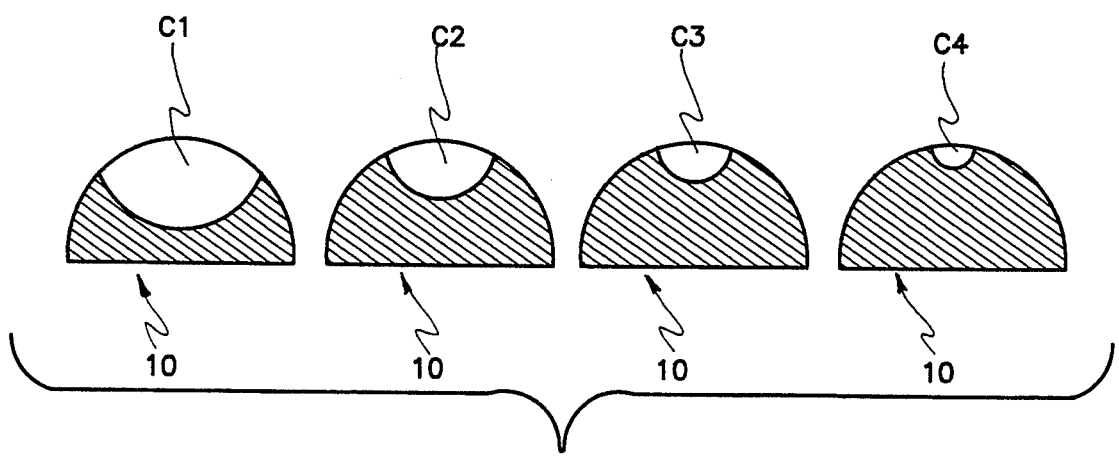
FIG. 4 is a transverse section of a series of dies showing differing volumes of four cavities in a schematic fashion.
Figure 5:
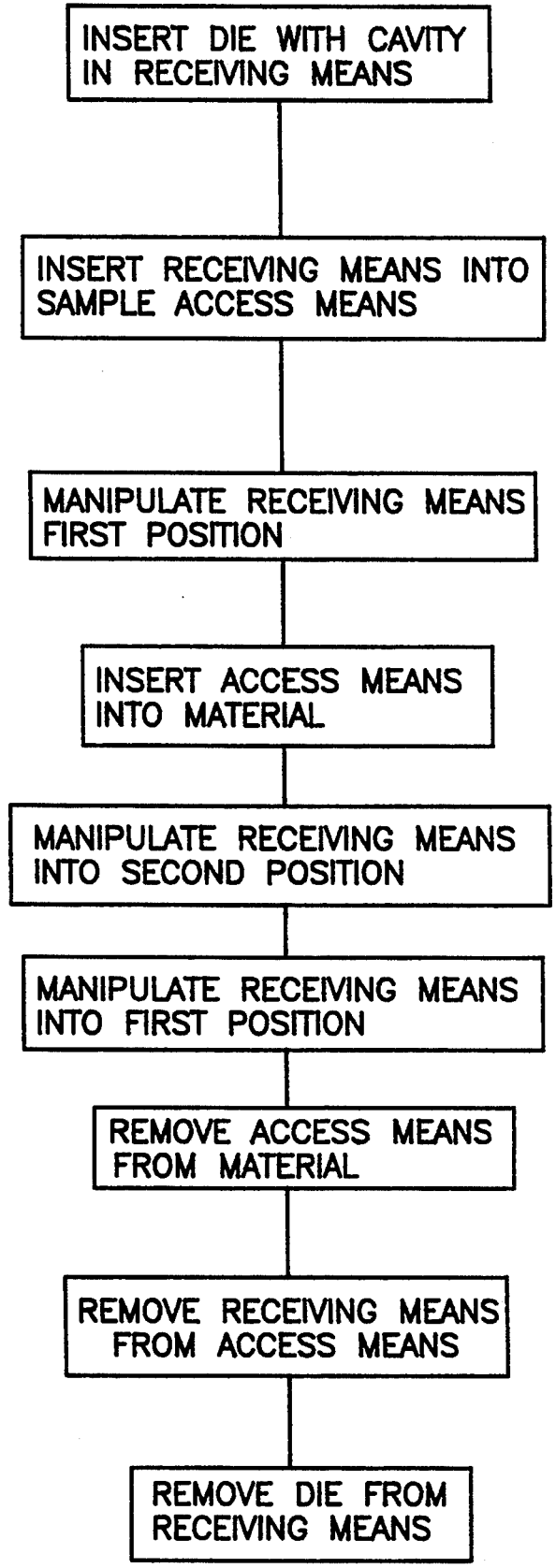
FIG. 5 is a block diagram of the method of the invention.

FIG. 4, a series of dies 10 are shown in a transverse section, showing in schematic form a series of dies 10 having cavities C1, C2, C3, and C4 of varying sizes.

It is to be understood that the present invention is not limited to the sole embodiment described above, but encompasses any and all embodiments within the scope of the following claims.

I claim:

1. A sampling device for obtaining precise volumetric samples from a powder blend comprising:
   a plurality of sampling dies, each said die including means for defining a cavity therein, each cavity having a predetermined volume, wherein at least one cavity includes adjustment means to vary the volume of said cavity;
   a plurality of mutually engageable die receiving means for snugly receiving at least one of said sampling dies and for holding said dies in a fixed relationship, said die receiving means further including a manipulable die displacement means; and
   a sample access means having an inner wall and an outer sample access area, said access means dimensioned and configured to receive said die receiving means such that said receiving means can be manipulated by said displacement means into a first and a second position, said access means including a travel stop for retaining said die receiving means in a predetermined relationship relative to said access means, there further being wall means to retain said sampling dies, such that in said first position said inner wall retains and encloses said cavity so that no communication exists between said cavities and said outer sample access area, and means to define a plurality of apertures such that said apertures are not in alignment with said sampling dies, and that in said second position, said inner wall retains said sampling dies so there is communication between said cavities and said outer sample access area through said apertures; whereby
   said die receiving means and said dies are held in said predetermined relationship within said sample access means, and after insertion of said device in a powder blend for sampling, said displacement means is manipulated to bring said cavities from said first enclosed position into in said second open position such that a sample of a specific predetermined volume enters each of said cavities, and thereafter, said displacement means are further manipulated to bring said cavities into said first enclosed configuration, for removal from the sample and testing of the obtained, predetermined volumes of samples.

2. The sampling device according to claim 1 wherein said adjustment means include an adjustable wall.

3. The sampling device according to claim 1, wherein said manipulable die displacement means comprises a handle member.

4. The sampling device according to claim 1, wherein said sample access means comprise a generally cylindrical hollow tube having an open end for the insertion of said die receiving means.

5. The sampling device according to claim 1, wherein said travel stop for said receiving means comprises a reduced diameter portion defined within said tube at a predetermined location.

6. A sampling device for obtaining precise volumetric samples from a powder blend comprising:
   a plurality of sampling dies, each said die including means for defining a cavity therein, each cavity having a predetermined volume;
   a plurality of mutually engageable die receiving means for snugly receiving at least one of said sampling dies said dies in a fixed relationship, wherein said plurality of die receiving means comprise a plurality of generally cylindrical members having cutout portions therein, said cutout portions correspondingly configured with said dies such that said dies are received and secured therein, said die receiving means further including a manipulable die displacement means; and
   a sample access means having an inner wall and an outer sample access area, said access means dimensioned and configured to receive said die receiving means such that said receiving means can be manipulated by said displacement means into a first and a second position, said access means including a travel stop for retaining said die receiving means in a predetermined relationship relative to said access means, there further being wall means to retain said sampling dies, such that in said first position said inner wall retains and encloses said cavity so that no communication exists between said cavities and said outer sample access area, and means to define a plurality of apertures such that said apertures are not in alignment with said sampling dies, and that in said second position, said inner wall retains said sampling dies so there is communication between said cavities and said outer sample access area through said apertures; whereby
   said die receiving means and said dies are held in said predetermined relationship within said sample access means, and after insertion of said device into a powder blend for sampling, said displacement means is manipulated to bring said cavities from said first enclosed position into said second open position such that a sample of a specific, predetermined volume enters each of said cavities, and thereafter, said displacement means are further manipulated to bring said cavities into said first enclosed configuration, for removal from the sample and testing of the obtained, predetermined volumes of samples.

7. The sampling device according to claim 4, wherein said manipulable die displacement means comprise a handle member.

8. The sampling device according to claim 4, wherein said sample access means comprise a generally cylindrical hollow tube having an open end for the insertion of said die receiving means.

9. The sampling device according to claim 4, wherein said travel stop for said receiving means comprises a reduced diameter portion defined within said tube at a predetermined location.

* * * * *

UNITED STATES PATENT AND TRADEMARK OFFICE
CERTIFICATE OF CORRECTION

PATENT NO. : 5,337,620
DATED : August 16, 1994
INVENTOR(S) : Sanyasi Kalidindi

It is certified that error appears in the above-indentified patent and that said Letters Patent is hereby corrected as shown below:

On the title page, item [76]: inventor last name should read --Kalidindi--.

Signed and Sealed this

Eighteenth Day of October, 1994

Attest:

BRUCE LEHMAN

*Attesting Officer*     *Commissioner of Patents and Trademarks*